(12) United States Patent
Verboom et al.

(10) Patent No.: US 8,114,906 B2
(45) Date of Patent: Feb. 14, 2012

(54) ESSENTIAL FATTY ACIDS IN THE TREATMENT AND/OR INHIBITION OF DEPRESSION IN PATIENTS WITH CORONARY HEART OR ARTERY DISEASE

(75) Inventors: Cees-Nico Verboom, Wietze (DE); Rainer Oelze, Hannover (DE)

(73) Assignee: Abbott Products GmbH, Hannover (DE)

( * ) Notice: Subject to any disclaimer, the term of this patent is extended or adjusted under 35 U.S.C. 154(b) by 0 days.

(21) Appl. No.: 11/106,482

(22) Filed: Apr. 15, 2005

(65) Prior Publication Data

US 2005/0245610 A1    Nov. 3, 2005

Related U.S. Application Data

(60) Provisional application No. 60/562,560, filed on Apr. 16, 2004.

(30) Foreign Application Priority Data

Apr. 16, 2004 (EP) .................................... 04101578

(51) Int. Cl.
*A01N 37/06* (2006.01)
*A61K 31/22* (2006.01)

(52) U.S. Cl. ...................................................... 514/549

(58) Field of Classification Search .................. 514/549
See application file for complete search history.

(56) References Cited

U.S. PATENT DOCUMENTS 5,760,081 A * 6/1998 Leaf et al. ...................... 514/560
2003/0060509 A1 * 3/2003 Elswyk .......................... 514/560

FOREIGN PATENT DOCUMENTS

EP  1157 692  * 11/2001

OTHER PUBLICATIONS

Peet (advances in psychiatric Treatment (2002), vol. 8, pp. 223-229.*
Carney et al. (Pyscological distress as a risk factor for stroke-related mortality)Stroke 2002;33;5-6.*
Clouse et al Depression and coronary heart disease in women with diabetes, Phycosomatic medicine 65: 376-383 (2003).*
Woodman et al., Atherosclerosis 166 (2003) 85-93.*
WebMD www.webmd.com, pp. 1-5, 2005 (evidece only).*
Peet et al, Arch. Gen. Phychiatry, 59 2002, 913-919.*
Horribin et al. Prostaglandins, leukotrienes and Essential Fatty Acids 60(4),217-234, 1999.*
Horrocks et al. Pharmacological Research 40 (3),1999, 211-225.*
www.diagnose-me.com (2002) 4 pages.*
Turner, N. et al. "Docosahexaenoic acid (DHA) content of membranes determines molecular activity of the sodium pump: implications for disease states and metabolism", Naturwissenschaften vol. 90, No. 11, Oct. 10, 2003, pp. 521-523, Abstract.
Kuan-Pin, Su et al. "Omega-3 fatty acids in major depressive disorder; a preliminary doubleblind, placebo-controlled trial", European Neuropsychopharmacology, vol. 13, Jan. 28, 2003, pp. 26271, Abstract.
Hamzaki, T. et al."Docosahexaenoic acid does not affect aggression of normal volunteers under nonstressful conditions. A randomized, placebo-controlled double-blind study" Lipids, vol. 33, No. 7, 1998, pp. 663667.
Ayorinde, F.O. et al. "Matrix-assisted Laser Desorption/Ionization Time-of-flight Mass Spectrometry of Cod Liver Oil and Effect of Analyte/Matrix Concentrations on Signal Intensities", Rapid Communications in Mass Spectrometry., vol. 13, Jul. 7, 1999, pp. 17621769, Abstract.
Marangell et al., Inform., 11: 878, 2000, abstract.
Marangell et al., "A Double-Blind, Placebo-Controlled Study of the Omega-3 Fatty Acid Docosahexaenoic Acid in the Treatment of Major Depression", Am. J. Psychiatry, 160: 5, 2003.

* cited by examiner

*Primary Examiner* — Brandon Fetterolf
*Assistant Examiner* — Shirley V Gembeh
(74) *Attorney, Agent, or Firm* — Crowell & Moring LLP

(57) ABSTRACT

A method of treating or inhibiting depression in a patient with cardiovascular disease, especially a patient suffering from coronary artery or vascular disease, the method including administering, preferably orally, to the patient a therapeutically effective amount of an essential fatty acid composition comprising preferably more than 25% by weight of eicosapentanoic acid ethyl ester (EPA), of docosahexaenoic acid ethyl ester (DHA), or of a mixture of eicosapentanoic acid ethyl ester (EPA) and docosahexaenoic acid ethyl ester (DHA), especially a mixture of EPA and DHA in an EPA/DHA ratio in the range from about 0.9 to about 1.5 at a dosage of from about 0.7 g to about 6 g per day.

4 Claims, No Drawings

ESSENTIAL FATTY ACIDS IN THE TREATMENT AND/OR INHIBITION OF DEPRESSION IN PATIENTS WITH CORONARY HEART OR ARTERY DISEASE

CROSS REFERENCE TO RELATED APPLICATIONS

This application claims priority from U.S. provisional patent application No. 60/562,560, filed Apr. 16, 2004, the entire disclosure of which is incorporated herein by reference. Priority is also claimed based on European patent application no. EP 04 10 1587.5, filed Apr. 16, 2004, which is likewise incorporated by reference.

BACKGROUND OF THE INVENTION

This invention relates to the use of a pharmaceutical composition containing essential fatty acid ethyl esters originating from fish oils, in particular as a high concentration mixture of ethyl esters of (20:5ω 3) eicosapentaenoic acid (EPA) and (22:6ω 3) docosahexaenoic acid (DHA) for the treatment and/or inhibition of depression in patients with coronary artery disease.

It is known that certain essential fatty acids contained in fish oil have a therapeutic effect in the prevention and treatment of cardiovascular disorders, such as in the treatment of hypertension, thrombosis, hypercholesterolemia, arteriosclerosis, cerebral infarction, prevention of sudden death in post myocardial infarction patients, improvement of endothelial function and hyperlipedemias. See, for example, U.S. Pat. Nos. 5,502,077; 5,656,667, and 5,698,594. The prevention of cardiovascular events, especially of mortality in patients who have survived the hospitalization phase of acute myocardial infarction (AMI), is described in the international patent application no. WO 00/48592.

The foregoing prior art in particular provides knowledge about the utility of fatty acids belonging to the ω-3 family, more specifically (20:5ω 3) eicosapentaenoic acid (EPA) and (22:6ω 3) docosahexaenoic acid (DHA), in treating the aforementioned disorders.

The fatty acid EPA, being a precursor of PGI3 and TxA3, exerts a platelet aggregation preventing effect and an antithombotic effect that can be ascribed to inhibition of cyclooxygenase (similar effect to that of aspirin) and/or to competition with arachidonic acid for this enzyme, with consequent reduction in the synthesis of PGE2 and TxA2, which are well known platelet aggregating agents.

On the other hand the fatty acid DHA is the most important component of cerebral lipids in man and furthermore, being a structural component of the platelet cell, it intervenes indirectly in increasing platelet fluidity, thus playing an important role in antithombotic activity.

International patent application WO 89/11521, the disclosure of which is incorporated herein by reference, describes in particular an industrial process for extracting mixtures having a high content of poly-unsaturated acids, including EPA and DHA and their ethyl esters, from animal and/or vegetable oils. Mixtures of fatty acids, especially EPA/DHA, obtained according to WO 89/11521, are reported to be particularly useful in the treatment of cardiovascular diseases.

However, current methods of treatment used in human therapy have been shown to be insufficient in patients with coronary artery disease.

Recently new risk factors for coronary artery disease have been identified, among them depression. Major depressive disorders, as well as depression symptoms, are associated with higher rates of cardiovascular morbidity and mortality. Moreover, once the ischemic heart disease is established, the risk of suffering a fatal cardiac event is increased. Severe ventricular arrhythmias resulting in sudden cardiac death appear to be the leading cause of mortality in patients with depression. In addition, patients with anxiety and depressive disorders have been shown to have reduced heart rate variability. This finding may have important prognostic implications because low heart rate variability is a powerful predictor of sudden cardiac death.

There is substantial evidence that major depression is associated with alterations in omega-3 acids status. A significant depletion of red cell membrane omega-3 fatty acids has been reported in major depression. Another study reported a negative correlation between severity of depression and both red blood cell membrane content of omega-3 fatty acids and dietary intake of these polyunsaturated fatty acids. Supplementation with EPA and DHA is known to increase the content of these unsaturated fatty acids in erythrocyte membranes. Studies in post-myocardial infarct patients have demonstrated that supplementation with DHA and EPA improves heart rate variability.

However, currently there are no safe and effective treatments known to inhibit depression in patients with cardiovascular disease and hardly any other treatments of depression in patients with cardiovascular disease. One study with sertraline showed beneficial effects in post-myocardial patients with concomitant depression. It is well known that patients with cardiovascular diseases and depression are at a substantially increased risk of cardiovascular events and death.

Therefore, there is still a substantial need for improved and effective treatment and/or inhibition with drugs, in particular for preventing these recurrences in patients suffering from both cardiovascular diseases and depression, and for the effective treatment of depression in these patients.

SUMMARY OF THE INVENTION

Thus, it is an object of the invention to provide an improved method of treating or inhibiting depression in a patient suffering from coronary disease.

Another object of the present invention is to provide such an improved and effective method of treatment and/or inhibition of said patients with an effective drug, and in particular preventing the aforementioned recurrences in patients suffering from both cardiovascular diseases and depression, and/or for treatment of depression in these patients.

These and other objects are achieved in accordance with the present invention by providing a method for treating or inhibiting depression in a patient with cardiovascular disease, said method comprising administering to said patient a therapeutically effective amount of an essential fatty acid composition comprising eicosapentanoic acid ethyl ester (EPA), docosahexaenoic acid ethyl ester (DHA), or a mixture of eicosapentanoic acid ethyl ester (EPA) and docosahexaenoic acid ethyl ester (DHA).

This invention, therefore, comprises a novel method for treating and/or inhibiting depression in patients with cardiovascular disease, in particular in patients with coronary heart and/or coronary artery or vascular disease, preferably in patients with coronary artery or vascular disease, comprising administering to the patient a therapeutically effective amount of a pharmaceutical composition containing essential fatty acids containing a high content of eicosapentanoic acid ethyl ester (EPA), of docosahexaenoic acid ethyl ester (DHA) or of a mixture of eicosapentanoic acid ethyl ester (EPA) and docosahexaenoic acid ethyl ester (DHA). Preferably, the composition contains a high concentration of a mixture of eicosapentanoic acid ethyl ester (EPA) and docosahexaenoic acid ethyl ester (DHA).

For ease of description "EPA-ethyl ester" and "DHA-ethyl ester" will be also be referred to hereinafter as "EPA" and "DHA". A high content of EPA-ethyl ester or DHA-ethyl ester or a high concentration of a mixture thereof, is to be understood to contain at least 20% by weight EPA or DHA, or at least 20% by weight of a mixture of EPA and DHA.

DETAILED DESCRIPTION

The present invention thus relates to a novel method for treating and/or inhibiting depression in patients with cardiovascular disease, in particular in patients with coronary heart and/or coronary artery or vascular disease, preferably in patients with coronary artery or vascular disease, comprising administering to the patient a therapeutically effective amount of a pharmaceutical composition containing essential fatty acids having a high content of eicosapentanoic acid ethyl ester (EPA), or docosahexaenoic acid ethyl ester (DHA), or a high content of a mixture of eicosapentanoic acid ethyl ester (EPA) and docosahexaenoic acid ethyl ester (DHA). Preferably, the composition contains a high concentration of a mixture of eicosapentanoic acid ethyl ester (EPA) and docosahexaenoic acid ethyl ester (DHA).

A high content of EPA-ethyl ester or DHA-ethyl ester or a high concentration of a mixture thereof, is to be understood to comprise at least 20% by weight EPA or DHA, or at least 20% by weight of a mixture of EPA and DHA.

In a preferred embodiment, this invention pertains to the use of essential fatty acids containing a mixture of eicosapentanoic acid ethyl ester (EPA) and docosahexaenoic acid ethyl ester (DHA) for the treatment and/or inhibition of depression in patients with cardiovascular disease, especially in patients with coronary heart and/or coronary artery or vascular disease, where the content of EPA and DHA in such mixture is greater than 25% by weight.

An essential fatty acid with high content in EPA or DHA, according to the present invention, preferably contains more than 25% by weight (by weight), in particular from about 60 to about 100% of such ester. These compounds can be obtained by known methods.

In an essential fatty acid with a high concentration of a mixture of EPA and DHA, preferably such a mixture has a content of EPA and DHA greater than 25% by weight, in particular from about 30 to about 100% by weight, especially preferably about 85% by weight. In the EPA/DHA mixture, EPA preferably is present in a percentage from about 40 to 60% by weight and DHA, preferably in a percentage from about 25 to about 45-50%. In any case, the preferred EPA/DHA ratio in such a EPA/DHA mixture is from about 0.9 to about 1.5.

Pharmacology

Cardiovascular disease is a leading cause of morbidity and disability in the United States with an estimated six million people having symptomatic coronary heart disease. Major depression is occurring at a younger age and a higher incidence than it used to occur. Alterations in phospholipids and cholesterol, which are structural components of all cell membranes in the brain, may induce changes in membrane microviscosity and, consequently in various neurotransmitter systems, which are thought to be related in the pathophysiology of depression, e.g. serotonin, and (nor-) adrenaline. Major depression and depressive symptoms, although commonly encountered in medical populations, are frequently underdiagnosed and untreated in patients with cardiovascular disease. In patients with coronary heart disease, the prevalence of major depression is nearly 20% and the prevalence of minor depression is approximately 27%.

Depression (major depressive disorders as well as depressive symptoms) is associated with higher rates of cardiovascular morbidity. The prognosis after a coronary heart disease event is poorer in depressed patients than in non-depressed patients. Patients with depression are less likely to follow recommendation to reduce cardiac risk during recovery from a myocardial infarction. In major depression, there is a decreased ω-3 fractions in cholesterol esters and an increased C20:4 ω 6/C20:5 ω 3 ratio in cholesterol esters and phospholipids.

Depression is an important independent predictor of death after coronary artery bypass surgery. Survival analyses, controlling for age, sex, number of grafts, diabetes, smoking, left ventricular ejection fraction, and previous myocardial infarction, showed that patients with moderate to severe depression at baseline (adjusted hazard ration (HR) 2.4, p=0.001) and with mild or moderate to severe depression that persisted from baseline to 6 months (adjusted HR 2.2) had higher rates of death than did those without depression. Mild to moderate levels of depressive symptoms are also in patients after an acute myocardial infarction associated with decreased survival. Highest mortality rates were observed in patients with most severe depressive symptoms. However, compared with those without depression, higher mortality was also observed at very low levels of depressive symptoms not generally considered clinically significant.

Increased mortality after a myocardial infarction is seen in both females and males. The one-year cardiac mortality is approximately 3 times higher in depressed females and 2.5 times higher in depressed males than in non-depressed females and non-depressed males, respectively. Preliminary research has shown that, in addition to the survival risks associated with post-myocardial depression, there are increased health care costs to both readmissions and outpatient contacts among depressed patients who survived the first post-myocardial infarction year.

The reasons why patients with coronary heart disease and depression have an increased mortality and morbidity are not fully understood. However, there are indications that in depression there is an abnormal intake or metabolism of essential fatty acids in conjunction with decreased formation of cholesteryl esters. The arachidonic acid to eicosapentaneoic acid ratio in blood correlates positively with the clinical symptoms of depression. Also a significant negative correlation is found between the EPA content in erythrocytes the severity of depression. Alterations in phospholipids and cholesterol, which are structural components of all cell membranes in the brain, may induce changes in membrane microviscosity and, consequently, in various neurotransmitter systems like in serotonin and (nor-) adrenaline. It is well known that these neurotransmitters play an important role in the pathophysiology of depression. Finally, the decreased food intake and weight loss, accompanying severe depression could lead to changes in fatty acid composition of serum phospholipids and cholesteryl esters, which could on their own affect membrane fluidity and inflammatory responses.

The efficacy of the treatment in accordance with the invention is demonstrated by indirect pre-clinical and clinical evidence:
1. Ingestion of large effects of ω-3 fatty acids is associated with a general dampening of signal transduction pathways associated with phosphatidylinisitol, arachidonic acid, and other systems.

2. DHA is involved in dopamine and serotonin metabolism in the developing rat brain.
3. Serotonergic and other neurochemical actions of ω-3 fatty acids in animals suggest anti-depressant activity.
4. Epidemiological data show that the national rates of major depression and bipolar disorder across different countries vary directly with fish consumption.
5. Epidemiological studies have demonstrated a correlation between plasma fatty acid composition and depression in the elderly.
6. In bipolar disorders, over-activity of cell signal transduction may be involved in the pathophysiology.
7. Patients with major depressive episodes showed a significant decrease in red blood cell membrane DHA and EPA levels.
8. Omega-3 fatty acids possess mood stabilizing effects in major depression and other neuro-psychiatric disorders.
9. Addition of EPA to treatment resistant depression was associated with symptoms remission, structural brain changes and a reduced neuronal phospholipids turnover.
10. Omacor, a high concentration mixture of EPA and DHA, increases the red blood cell membrane EPA and DHA content.

The foregoing evidence shows that the present invention provides a new and valuable therapeutic method for treating and/or inhibiting depression in patients with cardiovascular disease, in particular in patients with coronary heart and/or coronary artery or vascular disease. Accordingly, this invention provides a method for treating and/or inhibiting depression in patients with coronary vascular disease, and in particular in patients with coronary heart and/or coronary artery or vascular disease, comprising administering to such patient a therapeutically effective amount of a composition comprising essential fatty acids with a high content of EPA-ethyl ester or DHA-ethyl ester or a high concentration of a mixture thereof.

The essential fatty acids according to the invention can have a high content, for instance more than 25% by weight, of either EPA or DHA or a mixture thereof. However, EPA and DHA-ethyl ester are preferably present as a mixture thereof with a content of EPA and DHA higher than 25% by weight, in particular from about 30 to about 100% by weight, especially preferably about 85% by weight Based on the available evidence, according to a preferred aspect of the invention, the dosage of an essential fatty acid containing an EPA and DHA mixture with 85% by weight titer for oral administration to a patient may vary from about 0.7 g to about 6 g daily, preferably about 1 g daily.

This amount of product as EPA and DHA mixture (or amount of EPA alone or DHA alone) may be administered in several divided doses throughout the day, or preferably in a single administration, in order to achieve the desired blood concentration level of the active agent(s). Obviously it is at the discretion of the physician to adjust the quantity of product to be administered depending on the age, weight and general condition of the patient.

The medicament, e.g. in the form of a pharmaceutical composition, according to this invention can be prepared according to known methods in the art. The preferred route of administration is the oral one, however, leaving alternative routes of administration, such as the parenteral route, to the discretion of the physician.

EXAMPLES

The following examples illustrate preferred formulations for oral administration, but are not intended to limit the scope of the invention in any way.

Gelatin Capsules

According to known pharmaceutical techniques, capsules having the following composition and containing 1 g of active ingredient (EPA and DHA, 85% titer) per capsule are prepared.

| Formulation 1 | |
| --- | --- |
| EPA-ethyl ester | 525 mg/capsule |
| DHA-ethyl ester | 315 mg/capsule |
| d-alpha tocopherol | 4 IU/capsule |
| gelatin | 246 mg/capsule |
| glycerol | 118 mg/capsule |
| red iron oxide | 2.27 mg/capsule |
| yellow iron oxide | 1.27 mg/capsule |

| Formulation 2 | |
| --- | --- |
| Ethyl esters of polyunsaturated fatty acids | 1000 mg |
| with content in ethyl esters of w-3 poly-unsaturated esters (eicosapentaenoic EPA, docosahexaenoic DHA) | 850 mg |
| d-1-α-tocopherol | 0.3 mg |
| gelatin succinate | 233 mg |
| glycerol | 67 mg |
| sodium p-oxybenzoate | 1.09 mg |
| sodium propyl p-oxobenzoate | 0.54 mg |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for treating or inhibiting depression in a patient with coronary heart disease or coronary artery disease, said method consisting of orally administering to said patient a therapeutically effective dosage of from 0.7 g to 6 g per day of an essential fatty acid composition comprising a mixture of eicosapentanoic acid ethyl ester (EPA) and docosahexaenoic acid ethyl ester (DHA) in an EPA/DHA ratio in the range from 0.9 to 1.5.

2. A method according to claim 1, wherein said composition contains more than 25% by weight of the mixture of EPA and DHA.

3. A method according to claim 1, wherein said composition contains from 30 to 100% by weight of the mixture of EPA and DHA.

4. A method according to claim 3, wherein said composition contains 85% by weight of the mixture of EPA and DHA.

* * * * *